United States Patent [19]
Hamilton et al.

[11] Patent Number: 5,871,607
[45] Date of Patent: *Feb. 16, 1999

[54] MATERIAL HAVING A SUBSTANCE PROTECTED BY DEFORMABLE STANDOFFS AND METHOD OF MAKING

[75] Inventors: Peter W. Hamilton, Cincinnati; Kenneth S. McGuire, Wyoming, both of Ohio

[73] Assignee: The Procter & Gamble Company, Cincinnati, Ohio

[*] Notice: The term of this patent shall not extend beyond the expiration date of Pat. No. 5,662,758.

[21] Appl. No.: 744,850

[22] Filed: Nov. 8, 1996

Related U.S. Application Data

[63] Continuation-in-part of Ser. No. 584,638, Jan. 10, 1996, Pat. No. 5,662,758.

[51] Int. Cl.$^6$ ....................................................... B32B 31/00
[52] U.S. Cl. .......................... 156/221; 156/230; 156/235; 156/306.3; 427/208.6; 428/180
[58] Field of Search .................................... 156/221, 230, 156/235, 306.3; 427/208.6; 428/180

[56] References Cited

U.S. PATENT DOCUMENTS

| | | |
|---|---|---|
| 2,338,749 | 1/1944 | Wilbur . |
| 2,861,006 | 11/1958 | Salditt . |
| 3,018,015 | 1/1962 | Agriss et al. ........................... 428/180 |
| 3,312,005 | 4/1967 | McElroy . |
| 3,386,846 | 6/1968 | Lones . |
| 3,554,835 | 1/1971 | Morgan . |
| 3,592,722 | 7/1971 | Morgan . |
| 3,853,129 | 12/1974 | Kozak . |
| 3,901,237 | 8/1975 | Cepuritis et al. . |
| 3,937,221 | 2/1976 | Tritsch . |
| 3,943,609 | 3/1976 | Egan, Jr. . |
| 3,967,624 | 7/1976 | Milnamow . |
| 4,023,570 | 5/1977 | Chinai et al. . |
| 4,054,697 | 10/1977 | Reed et al. . |
| 4,061,820 | 12/1977 | Magid et al. . |

(List continued on next page.)

FOREIGN PATENT DOCUMENTS

| | | |
|---|---|---|
| 570960 | 12/1961 | Belgium . |
| 0 037 101 A1 | 10/1981 | European Pat. Off. . |
| 0 623 332 A1 | 9/1994 | European Pat. Off. . |
| 0 621 082 A1 | 10/1994 | European Pat. Off. . |
| 1 315 903 | 4/1963 | France . |
| 1429312 | 2/1966 | France . |
| 3-002292 | 1/1991 | Japan . |
| 7-246216 | 9/1995 | Japan . |
| 975783 | 11/1964 | United Kingdom . |
| 1069445 | 5/1967 | United Kingdom . |
| WO 92/00187 | 1/1992 | WIPO . |
| WO 95/11945 | 5/1995 | WIPO . |
| WO 95/31225 | 11/1995 | WIPO . |
| WO9619173 | 6/1996 | WIPO . |
| WO 96/41604 | 12/1996 | WIPO . |
| WO 97/18276 | 5/1997 | WIPO . |

*Primary Examiner*—John J. Gallagher
*Attorney, Agent, or Firm*—William Scott Andes

[57] ABSTRACT

A substance delivery system has a three dimensional structure with outermost surface features and spaces for containing a substance. The substance has a level below the outermost surface features such that the substance is protected from inadvertent contact with external surfaces. The substance remains protected until the three dimensional structure is sufficiently deformed into a substantially two dimensional structure and the substance is thereby exposed to contact an external surface without compliance of the external surface being necessary. Deforming is preferably achieved by a compression force, wherein the outermost surface features of the three dimensional structure deform in a direction of the compression force. A method of making the three dimensional material includes the steps of coating a substance onto a forming surface, transferring the coating of substance from the forming surface to a piece of material, and forming the piece of material into a three dimensional structure on the forming surface while the substance is in contact with the forming surface.

21 Claims, 4 Drawing Sheets

U.S. PATENT DOCUMENTS

| | | |
|---|---|---|
| 4,067,337 | 1/1978 | Ness . |
| 4,181,752 | 1/1980 | Martens et al. . |
| 4,273,889 | 6/1981 | Yamazaki et al. . |
| 4,303,485 | 12/1981 | Levens . |
| 4,336,804 | 6/1982 | Roeder . |
| 4,337,772 | 7/1982 | Roeder . |
| 4,342,314 | 8/1982 | Radel et al. . |
| 4,376,440 | 3/1983 | Whitehead et al. . |
| 4,392,897 | 7/1983 | Herrington . |
| 4,397,905 | 8/1983 | Dettmer et al. . |
| 4,410,130 | 10/1983 | Herrington . |
| 4,460,634 | 7/1984 | Hasegawa . |
| 4,508,256 | 4/1985 | Radel et al. . |
| 4,509,908 | 4/1985 | Mullane, Jr. . |
| 4,514,345 | 4/1985 | Johnson et al. . |
| 4,519,095 | 5/1985 | Clayton . |
| 4,528,239 | 7/1985 | Trokhan . |
| 4,556,595 | 12/1985 | Ochi . |
| 4,576,850 | 3/1986 | Martens . |
| 4,578,069 | 3/1986 | Whitehead et al. . |
| 4,587,152 | 5/1986 | Gleichenhagen et al. . |
| 4,655,761 | 4/1987 | Grube et al. . |
| 4,695,422 | 9/1987 | Curro et al. . |
| 4,699,622 | 10/1987 | Toussant et al. . |
| 4,743,242 | 5/1988 | Grube et al. . |
| 4,778,644 | 10/1988 | Curro et al. . |
| 4,839,216 | 6/1989 | Curro et al. . |
| 4,894,275 | 1/1990 | Pelzer . |
| 4,946,527 | 8/1990 | Battrell . |
| 4,959,265 | 9/1990 | Wood et al. . |
| 5,008,139 | 4/1991 | Ochi et al. . |
| 5,080,957 | 1/1992 | Leseman et al. . |
| 5,098,522 | 3/1992 | Smurkoski et al. . |
| 5,141,790 | 8/1992 | Calhoun et al. . |
| 5,176,939 | 1/1993 | Shepherd . |
| 5,221,276 | 6/1993 | Battrell . |
| 5,245,025 | 9/1993 | Trokhan et al. . |
| 5,246,762 | 9/1993 | Nakamura . |
| 5,269,776 | 12/1993 | Lancaster et al. . |
| 5,273,805 | 12/1993 | Calhoun et al. ......................... 428/180 |
| 5,275,588 | 1/1994 | Matsumoto et al. . |
| 5,296,277 | 3/1994 | Wilson et al. . |
| 5,324,279 | 6/1994 | Lancaster et al. . |
| 5,342,344 | 8/1994 | Lancaster et al. . |
| 5,344,693 | 9/1994 | Sanders . |
| 5,453,296 | 9/1995 | Lauritzen et al. ................... 427/208.6 |
| 5,458,938 | 10/1995 | Nygard et al. . |
| 5,487,929 | 1/1996 | Rusincovitch, Jr. et al. . |
| 5,514,122 | 5/1996 | Morris et al. . |
| 5,518,801 | 5/1996 | Chappell et al. . |
| 5,527,112 | 6/1996 | Dais et al. . |
| 5,575,747 | 11/1996 | Dais et al. . |
| 5,585,178 | 12/1996 | Calhoun et al. . |
| 5,589,246 | 12/1996 | Calhoun et al. . |
| 5,662,758 | 9/1997 | Hamilton et al. ....................... 156/221 |

MATERIAL HAVING A SUBSTANCE PROTECTED BY DEFORMABLE STANDOFFS AND METHOD OF MAKING

CROSS-REFERENCE TO RELATED APPLICATION

This is a continuation-in-part of our prior application, Ser. No. 08/584,638, filed Jan. 10, 1996, entitled COMPOSITE MATERIAL RELEASABLY SEALABLE TO A TARGET SURFACE WHEN PRESSED THEREAGAINST AND METHOD OF MAKING, now U.S. Pat. No. 5,662,758.

FIELD OF THE INVENTION

The present invention relates to a sheet-like material which is formed to have three dimensional surface features with spaces therein to contain a substance, and more particularly to such materials wherein the surface features prevent external surfaces from contacting the substance until forces exerted on the surface features cause them to deform. The present invention further relates to methods of making such sheet-like materials.

BACKGROUND OF THE INVENTION

There exist articles which are coated or impregnated with useful substances intended to be utilized when the article is contacted with a target surface. While there are advantages with having the substance present on or near the surface of such articles, there is often the drawback that the useful substance is unprotected and is subject to inadvertent contact before intended use. One broad category of such articles encompasses the area of tapes and labels.

In the art of tapes, labels, and other articles using pressure sensitive adhesive to adhere an adhesive coated surface to a target surface, there has been recognized the problem of premature sticking to the target surface. That is, before the adhesive coated surface can be properly positioned over a target surface, inadvertent contact of the adhesive with the target surface causes premature sticking at one or more locations, thereby inhibiting proper positioning. Premature sticking may also cause contamination or degradation of the adhesive prior to final positioning at the target surface.

Others have attempted to overcome this problem by providing standoffs on a material surface, between which adhesive elements are located. Standoffs include any means extending outwardly from an adhesive surface which is contacted first before the adhesive surface is exposed to contact by another surface. Protecting an adhesive from premature contact by another surface has been achieved by adding strips of polymer foam to form deformable standoffs on an adhesive surface, for example. Polymer foams, however, tend to spring back and exert a peel force on the adhesive bond to the target surface. Thus, a more aggressive adhesive may be required to overcome this undesirable peel force.

U.S. Pat. No. 5,141,790 to Calhoun et al. discloses one-time repositionable pressure sensitive tapes with an adhesive coated surface having clumps of particles spaced out on the adhesive to keep the adhesive from touching a target surface until the sheet is pressed against the target surface. The particles are smaller than the thickness of the adhesive layer so that when pressed, the particles sink below the surface of the adhesive and no longer provide their spacing function. Since adhesive may be the most expensive component of a tape, and since the overall surface is coated with a thick layer of adhesive, Calhoun et al. would offer an expensive solution.

U.S. Pat. No. 4,061,820 to Magid et al. discloses a foam with cells. The foam is compressed to open cell cavities at the foam surface so that pressure sensitive adhesive can be applied to the open cells. When the foam is released, the cells close and hide the adhesive. When the foam is pressed, the cells bring pressure sensitive adhesive to the surface for sticking the foam to a target surface. This too is believed to be an expensive solution to the problem, and defining continuous or interconnected patterns of adhesive would not be possible. Also, polymer foams provide undesirable spring back force, which acts to undo the adhesive bond to a target surface. Furthermore, in some applications transparency may be beneficial, such as for accurate placement, and the foam of Magid et al. would not be transparent.

U.S. Pat. No. 4,959,265 to Wood et al. discloses an adhesively coated substrate having bluntly pointed stems protruding beyond a layer of pressure sensitive adhesive. The back of this substrate may be bonded to a sanitary napkin. The napkin may then be installed onto a foraminous fabric by pressing to force the stems to penetrate the fabric to a depth where the fabric contacts the adhesive. By penetrating fabric, the stems significantly reinforce the adhesion of the fastener. The stems should be resistant to compression and bending, even thought they may be quite supple. The backing with its stems preferably is formed from a tough thermoplastic resin by cast molding or extrusion molding. The stems protrude 20 microns to 3 mm above the adhesive level, depending on the coarseness of the fabric to be penetrated. The adhesive area is preferably between 3 and 30 times the area occupied by the stems. Rigid target surfaces are obviously inoperable with Wood et al.

U.S. Pat. No. 5,344,693 to Sanders discloses a substrate having a plurality of non-interconnecting spacing means extending outwardly from an adhesive coated surface to space the surface from another surface until the surfaces are pressed together. The spacing means of Sanders is non-deformable. The spacing members are spaced up to 80 times the dimension of each spacer. Since few spacing members provide the standoff function, Sanders would need a stiff web between members as well as stiff members to prevent inadvertent adhesive contact. Stiffness in Sanders' configuration corresponds to thick, and therefore expensive materials. Sanders discusses his invention for use with reclosable bags. Sanders, like Wood et al., would not be compatible with rigid target surfaces where the members deform instead of the target surface.

A commonly assigned, co-pending U.S. patent application, Ser. No. 08/584,638, filed Jan. 10, 1996 by the same inventors as in the present application, discloses a film formed to have deformable hollow protrusions which are very closely spaced and a continuous layer of pressure sensitive adhesive located between the protrusions. This co-pending application is hereby incorporated herein by reference. The close spacing between protrusions enables the web material to be very thin and flexible yet resistant to inadvertent deformation because of the high density of standoffs per unit area. However, the co-pending application focuses on formed films which have pressure sensitive adhesive between protrusions. The same inventors have discovered much broader constructions for their new material, as well as alternative methods of making it.

Methods for making articles and surfaces having adhesive surfaces protected by standoffs are disclosed, for example, in U.S. Pat. No. 5,453,296 to Lauritzen et al. Lauritzen et al. describes methods for making a sanitary napkin which has a recessed adhesive pattern for attaching it to a user's undergarment. Lauritzen et al. forms depressions in a fluidimpervious barrier film. The depressions create raised areas in the barrier film on the side of the napkin which attaches to the undergarment. Adhesive is placed onto the barrier film side having the raised areas in discrete patterns between the raised areas. In an alternative, Lauritzen et al. applies adhesive to the tips of the raised areas of the barrier film and then inverts the raised areas to form depressions. The adhesive is thereby conveniently placed in the depressions. Lauritzen et al.'s discrete adhesive placement fails to enable an air-tight adhesive seal with a target surface, however.

Lauritzen et al. also notes that standoffs must be formed such that they are strong enough to protect the adhesive from inadvertent contact during shipping and storage, yet are deformable for activation. Lauritzen et al. states that sufficient rigidity is available from 0.03 inch (0.08 cm) to 0.06 inch (0.15 cm) thick foam. In one embodiment, conical depressions have diameters at their open ends of 0.1 inches (0.25 cm) to 0.5 inches (1.27 cm) and depths of 0.1 inches (0.25 cm) to 0.25 inches (0.64 cm). Such large depressions and thick foam preclude the ability to wind up the material in a compact roll for consumer delivery. Also, large sized standoffs provide greater opportunity for an interrupted seal instead of a continuous seal, especially when dealing with a narrow target surface. Smaller, more closely spaced standoffs increase the frequency of adhesive contact to the target surface to better approximates a continuous seal.

In still another Lauritzen et al. embodiment, a printing device transfers adhesive to a printing belt, which transfers adhesive to a release belt, and then to the barrier foam web. This system is used to first print a pattern of discrete patches of adhesive onto the barrier foam web. Then the foam web is registered with a vacuum plate. When each patch of adhesive is disposed above a recess in the forming plate, vacuum forms adhesive containing depressions. Because of registration requirements, the invention is believed limited to relatively large and well spaced standoffs. A fine pattern of very small standoffs would be difficult to make using Lauritzen et al.'s methods because registration for forming would require high accuracy. Lauritzen et al.'s methods are believed to limit material constructions to those having macro patterns of low number density of standoffs, compared to the micro pattern of high number density of standoffs of co-pending U.S. patent application, Ser. No. 08/584,638.

OBJECTS OF THE INVENTION

It is an object of the present invention to provide a three dimensional structure for containing a layer of substance therein, the substance staying therein until the three dimensional structure is deformed into a substantially two dimensional structure or otherwise activated to expose or release the substance.

It is another object of the present invention to provide a deformable, sheet-like material having a three dimensional surface comprising deformable protrusions, between which a substance is placed internal to the outermost ends of the protrusions in a continuous or interconnected pattern, wherein the substance is contactable by an external surface only after the protrusions are deformed to the level of the substance.

It is still another object of the present invention to provide a deformable material having deformable protrusions which is sufficiently thin to be wound onto compact rolls for storage and convenient packaging, yet having sufficient resistance to the deformation of protrusions in order to prevent premature deformation due to in-wound web tension, etc., while the material is stored in roll form.

It is yet another object of the present invention to provide a deformable material having deformable protrusions containing adhesive within or therebetween, which once deformed, stay deformed with minimal spring back so that adhesive exposed to contact with a target surface need not be overly aggressive in order to remain bonded to the target surface.

It is still another object of the present invention to provide a material including a very thin, finely patterned, three dimensional structure having a recessed substance layer, such that the material is substantially transparent or translucent so that it may be accurately positioned before deforming the structure to expose the substance layer.

It is a further object of the present invention to provide methods for making a very thin, finely patterned, three dimensional structure having a recessed substance layer accurately registered with deformable protrusions, wherein the method is capable of automated continuous motion or indexing motion for a continuous web format.

SUMMARY OF THE INVENTION

In the present invention, the term "substance" can mean a flowable substance which is substantially non-flowing prior to delivery to a target surface. "Substance" can also mean a material which doesn't flow at all, such as a fibrous or other interlocking material. "Substance" may mean a fluid or a solid. "Substance" is defined in this invention as any material capable of being held in open valleys and/or depressions of a three dimensional structure. Adhesives, electrostatics, mechanical interlocking, capillary attraction, surface adsorption, and friction, for example, may be used to hold the substances in the valleys and/or depressions. The substances may be permanently held in the valleys and/or depressions, or the substances may be intended to be released therefrom when exposed to contact with external surfaces or when the three dimensional structure is deformed, heated, or otherwise activated. Of current interest in the present invention include substances such as gels, pastes, foams, powders, agglomerated particles, prills, microencapsulated liquids, waxes, suspensions, liquids, and combinations thereof.

The spaces in the three dimensional structure of the present invention are normally open; therefore it is desirable to have substances stay in place and not run out of the structure without an activation step. The activation step of the present invention is preferably deformation of the three dimensional structure by compression. However, an activation step to cause substance to flow could be heating the material to above room temperature or cooling it below room temperature. Or it could include providing forces excessive of the earth's gravity. It could also include other deforming forces, such as tensile forces and combinations of these activation phenomena.

The term "deformable material" is intended to include foils, polymer sheets, cloth, wovens or nonwovens, paper, cellulose fiber sheets, co-extrusions, laminates, and combinations thereof. The properties of a selected deformable material can include, though are not restricted to, combinations or degrees of being: porous, non-porous, microporous, gas or liquid permeable, non-permeable, hydrophilic, hydrophobic, hydroscopic, oleophilic, oleophobic, high critical surface tension, low critical surface tension, surface pre-textured, elastically yieldable, plastically yieldable, electrically conductive, and electrically non-conductive.

In one aspect of the present invention, a substance delivery system comprises a three dimensional structure having outermost surface features and interconnected spaces for containing a substance. The substance has a level internal to the outermost surface features such that the substance is protected from inadvertent contact with external surfaces. A substance having substantial resistance to flow prior to delivery to a target surface occupies the interconnected spaces of the three dimensional structure. The substance remains protected until the three dimensional structure is sufficiently deformed into a substantially two dimensional structure and the substance is thereby exposed to contact an external surface without compliance of the external surface being necessary. The number density of the outermost surface features is greater than 200 outermost surface features/square inch or 31 surface features/square cm.

The three dimensional structure may be deformed by a compression force applied substantially perpendicular to a plane of the three dimensional structure, thereby causing the outermost surface features of said three dimensional structure to deform in a direction of the compression force. Alternatively, the three dimensional structure may be deformed by a tensile force applied substantially parallel to a plane of the three dimensional structure, thereby causing the outermost surface features of the three dimensional structure to deform in a direction substantially perpendicular to the plane. Also, the three dimensional structure may be deformed by a combination of a tensile force applied substantially parallel to a plane of the three dimensional structure and a compression force applied substantially perpendicular to the plane, thereby causing the outermost surface features of the three dimensional structure to deform substantially perpendicular to the plane.

In another aspect of the present invention, a method of making a three dimensional material having outermost surface features and having spaces for containing a substance internal to the outermost surface features, such that the substance is protected from inadvertent contact with external surfaces, comprises the steps of coating a substance onto a forming surface, transferring the coating of substance from the forming surface to a piece of material, and forming the piece of material into a three dimensional structure on the forming surface while the substance is still in contact with the forming surface. This method accurately registers the three dimensional structure with the substance so that the substance may be located within the spaces of the three dimensional structure internal to the outer most features thereof. A further step of this method may include providing the forming surface with a low critical surface tension so that the substance will adhere more readily to the piece of material than to the forming surface.

In yet another aspect of the present invention, a method of making a material, which has a substance protected from inadvertent contact with an external surface until the material is deformed, has a first step of coating a forming screen with a first substance. The forming screen has a top surface and a plurality of recesses therein. The coating step applies the first substance to the top surface without bridging the recesses. A second step includes introducing a piece of material, which has a first side and a second side, onto the forming screen such that the first side is in contact with the first substance on the top surface of the forming screen. The first substance preferentially adheres to the first side of the piece of material. A third step includes forming the piece of material to create a plurality of hollow protrusions extending from the first side into the recesses of the forming screen. The plurality of hollow protrusions are spaced apart by valleys into which the first substance is transferred from the forming screen. The plurality of hollow protrusions are accurately registered with the first substance by use of a common transfer and forming surface. The first substance forms an interconnected layer in the valleys between the protrusions.

The piece of material has a plurality of depressions on the second side corresponding to the plurality of hollow protrusions. The method may further comprise the step of injecting a second substance into the plurality of depressions on the second side of the piece of material. Alternatively, the method may further comprise the step of forming an aperture at the outermost end of each of the plurality of protrusions. The step of introducing the material onto the forming screen may include metering a web onto the forming screen or extruding the material directly onto the forming screen. The method may further comprise the step of removing the piece of material from the forming screen, preferably without leaving a residue of substance on the forming screen.

In still another aspect of the present invention, a method of making a material, which has a substance protected from inadvertent contact with an external surface until the material is deformed, has the first step of coating top surfaces of pins extending from a forming plate with a first substance. The pins are separated from each other by spaces. The coating step applies the first substance to the top surfaces of the pins without bridging across the spaces. A second step introduces a piece of material having a first side and a second side onto the pins such that the first side is in contact with the first substance on the top surface of the pins. The first substance preferentially adheres to the piece of material. A third step includes forming over the pins of the forming plate the piece of material to create a plurality of hollow protrusions extending from the second side. The plurality of hollow protrusions have depressions registered with the pins which have discrete spots of the first substance therein. The piece of material has an interconnected valley formed on the second side corresponding to the spaces between the pins.

The step of introducing the material onto the pins may include metering a web onto the pins or extruding the material directly onto the pins. As an alternative, the method may further comprise the step of forming an aperture in the interconnected valley between each of the plurality of protrusions. The method further comprises the step of removing the piece of material from the pins, preferably without leaving a residue of substance on the pins.

In a further aspect of the present invention, a piece of material has a substance therein protected from inadvertent contact with an external surface until the material is deformed. The piece of material comprises a piece of deformable material which has a first side formed to have a plurality of hollow protrusions separated by valleys. The plurality of hollow protrusions have outermost ends. The piece of material has a second side. The second side has a plurality of depressions therein corresponding to the plurality of hollow protrusions on the first side. The substance adheres to and partially fills the valleys between the plurality of hollow protrusions. The substance has a surface below the outermost ends of the plurality of hollow protrusions, so that when a portion of the first side of the piece of deformable film is placed against a target surface, the plurality of hollow protrusions prevent contact between the substance and the target surface until the portion is deformed at the target surface. Preferably, the plurality of protrusions deform by modes which are selected from the group consisting of inverting, crushing, and elongating. Preferably, in the inverting and/or crushing modes, each of the plurality of protrusions will not substantially deform until exposed to a pressure of at least 0.1 pounds per square inch (0.69 kPa).

The valleys contain a substance in at least a portion thereof. Preferably, the valleys have an interconnected layer of substance therein such that contact of the substance with the target surface forms a continuous pattern. The substance adheres preferentially to the first side of the piece of material. The plurality of depressions on the second side may also have a substance injected therein, which may be the same as or different than the substance transferred to the first side.

BRIEF DESCRIPTION OF THE DRAWINGS

While the specification concludes with claims which particularly point out and distinctly claim the present invention, it is believed that the present invention will be better understood from the following description of preferred embodiments, taken in conjunction with the accompanying drawings, in which like reference numerals identify identical elements and wherein:

DETAILED DESCRIPTION OF THE INVENTION

Referring now to the drawings, and more particularly to FIGS. 1–4, there is shown a preferred embodiment of the present invention, which provides a three dimensional sheetlike structure generally indicated as 10. Material 10 includes a deformed material 12 having hollow protrusions 14 and a layer of substance 16 located between protrusions 14. Protrusions 14 are preferably conical in shape with truncated or domed outermost ends 18. Protrusions 14 are preferably equally spaced in an equilateral triangular pattern, all extending from the same side of the material. Protrusions 14 are preferably spaced center to center a distance of approximately two protrusion base diameters or closer, in order to minimize the volume of valleys between protrusions and hence the amount of substance located between them. Preferably, the protrusions 14 have heights which are less than their diameters, so that when they deform, they deform by substantially inverting and/or crushing along an axis which is substantially perpendicular to a plane of the material. This protrusion shape and mode of deforming discourages protrusions 14 from folding over in a direction parallel to a plane of the material so that the protrusions cannot block substance between them from contact with a target surface.

Figure 1:
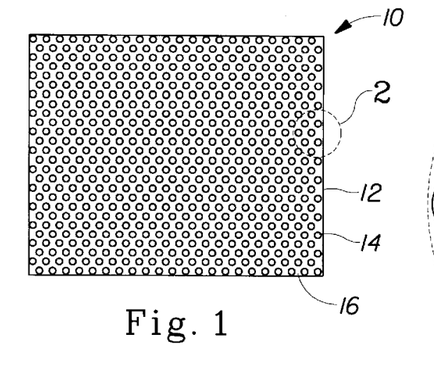
FIG. 1 is a top plan view of a preferred embodiment of the present invention, disclosing a piece of material having truncated conical protrusions surrounded by an interconnected pattern of substance.
Figure 2:
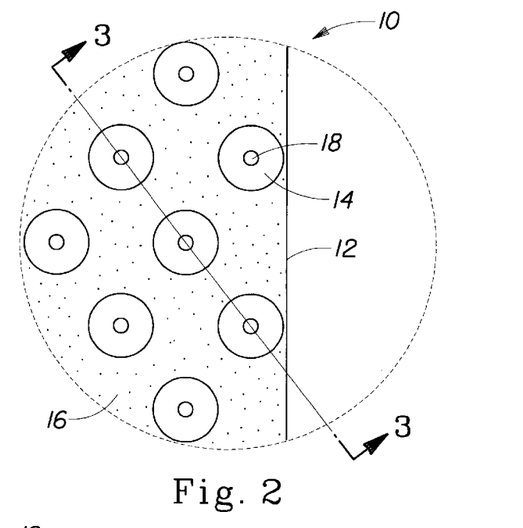
FIG. 2 is an enlarged partial top plan view thereof, showing an array of protrusions.
Figure 3:
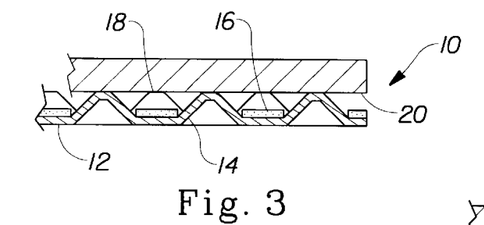
FIG. 3 is a sectioned elevation view thereof, taken along section line 3—3 of FIG. 2, showing the protrusions acting as standoffs for a substance layer between protrusions, such that a target surface contacting the outermost ends of the protrusions does not contact the substance layer.
Figure 4:
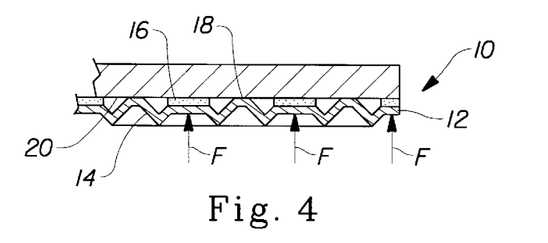
FIG. 4 is a sectioned elevation view thereof, similar to FIG. 3, showing the effect of pressing the material against the target surface, such that protrusions deform by substantially inverting and/or crushing to allow the substance layer between protrusions to contact the target surface.

FIG. 3 shows a target surface 20, which is smooth but which may have any surface topography, being spaced away from layer of substance 16 by outermost ends 18 of protrusions 14. Target surfaces may be any article surface made of any material, rigid, seem-rigid, or flexible. FIG. 4 shows target surface 20 contacting layer of substance 16 after protrusions 14 have been partially deformed under pressure applied to the non-substance side of material 12, as indicated by force F.

In a particularly preferred embodiment, conical protrusions 14 have a base diameter of about 0.015 inches (0.038 cm) to about 0.030 inches (0.076 cm), and more preferably about 0.025 inches (0.064 cm). They also have a center-to-center spacing of from 0.03 inches (0.08 cm) to 0.06 inches (0.15 cm), and more preferably about 0.05 inches (0.13 cm) spacing. This results in a high number density of protrusions. The more protrusion per unit area, the thinner the piece of material and protrusion walls can be in order to resist a given deformation force. In a preferred embodiment the number of protrusions per square inch exceeds 200 and the protrusions occupy from about 30% to about 70% of the protrusion side of the piece of material. They have a protrusion height of about 0.004 inches (0.010 cm) to 0.012 inches (0.030 cm), and more preferably about 0.006 inches (0.015 cm) height. The preferred material is 0.0003 inch (0.0076 mm) nominal thickness high density polyethylene (HDPE). Preferred layer of substance 16 is preferably a latex pressure sensitive adhesive about 0.001 inch (0.025 mm) thick. Even more preferably, layer of substance 16 may be about an 0.0005 inch (0.013 mm) thick layer to about an 0.002 inch (0.051 mm) thick layer of hot melt adhesive, specification no. Fuller HL-2115X, made by H. B. Fuller Co. of Vadnais Heights, Minn. Any adhesive can be used which suits the needs of the material application. Adhesives may be refastenable, releasable, permanent, or otherwise. The size and spacing of protrusions is preferably selected to provide a continuous adhesive path surrounding protrusions so that air-tight seals may be made with a target surface.

Film materials may be made from homogeneous resins or blends thereof. Single or multiple layers within the film structure are contemplated, whether co-extruded, extrusion-coated, laminated or combined by other known means. The key attribute of the film material is that it be formable to produce protrusions and valleys. Useful resins include polyethylene, polypropylene, PET, PVC, PVDC, latex structures, nylon, etc. Polyolefins are generally preferred due to their lower cost and ease of forming. Preferred material gauges are about 0.0001 inches (0.0025 mm) to about 0.010 inches (0.25 mm). More preferred gauges are from about 0.0002 inches (0.005 mm) to about 0.002 inches (0.051 mm). Even more preferred gauges are from about 0.0003 inches (0.0076 mm) to about 0.001 inches (0.025 mm).

Providing a film modulus of elasticity sufficiently high to minimize film stretch during use is beneficial to sealing material 10 to a target surface. Stretched film results in residual forces parallel to the plane of adhesive contact, which may cause a weak adhesive bond to break. The larger and more closely spaced the protrusions, the greater the likelihood of stretch occurring in a given film. Although elasticity in material 10 is believed to be undesirable for use as a container wrap which seals to a container, there are potentially many other uses for an elastic material containing a pattern of substance. Reducing the protrusion spacing to the closest possible spacing which is manufacturable may increase material stretch, but it may be beneficial in reducing the volume of substance between protrusions. Different applications for the formed material of the present invention will dictate ideal size and density of protrusions, as well as the selection of the substances used therewith.

Figure 5:
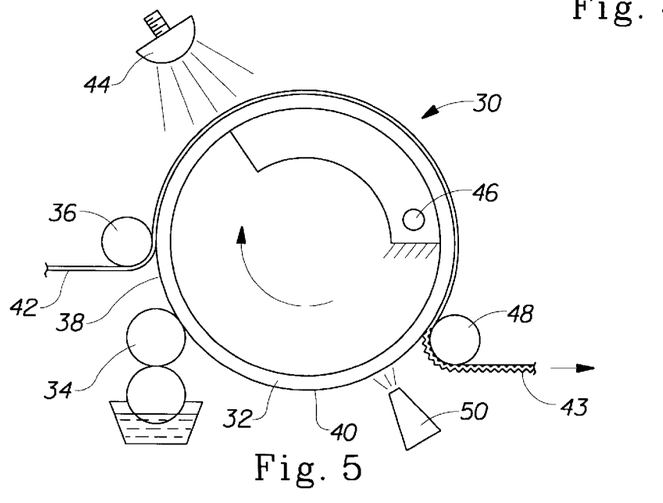
FIG. 5 is a schematic view of a method of making the material of the present invention, disclosing a continuous web entering a forming drum, which has a substance already applied to the surface of the drum, wherein the substance is thereafter transferred to the web prior to forming protrusions in the film.

FIG. 5 shows an automated process, generally indicated as 30, for making material 10, preferably a thin thermoplastic film containing a pressure sensitive adhesive. A forming screen 32 is curved to form a drum. A substance source and application system 34 are positioned upstream of an infeed idler roll 36. Substance application system 34 deposits a thin coating of a substance 38 onto an outer surface 40 of forming screen 32. Outer surface 40 is treated to have a low critical surface tension so that substance 38 will not strongly adhere to it upon cooling or drying. In a preferred embodiment, outer surface 40 is coated with a Series 21000 proprietary release coating made by and applied by Plasma Coatings of TN, Inc., located in Memphis, Tenn. It is believed that this coating is primarily an organo-silicone epoxy. As applied to a stainless steel forming screen used in the method of the present invention, this coating provides a critical surface tension of 18 dynes/cm. Other materials which may prove suitable for providing reduced critical surface tension include paraffins, silicones, PTFE's and the like.

Figure 12:
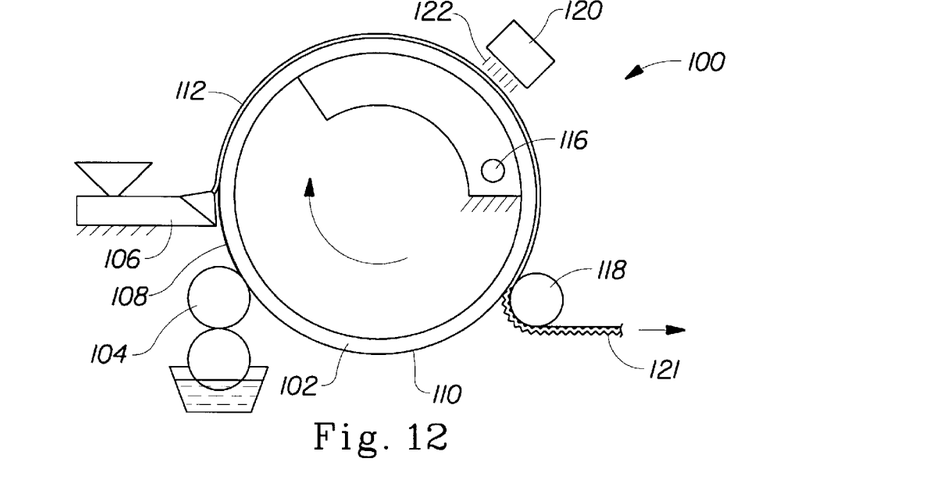
FIG. 12 is a schematic view of a method of making the material of the present invention, similar to the method shown in FIG. 5, except that a film is extruded directly onto the forming drum, and an ink jet device injects discrete portions of substance into depressions of the hollow protrusions from outside the drum.

The thin substance coating is about a 0.001 inch (0.025 mm) thick coating of pressure sensitive adhesive. Automated process 30 has a material web 42 threaded between infeed idler roll 36 and forming screen 32. In process 30, material web 42 is introduced onto top of layer of substance 38. Material web 42 is preferably attracted to layer of substance 38, at least sufficiently so that the substance has a greater affinity for material web 42 than for forming screen 32. For example, if material web 42 is a polyolefin film, corona treating the film will improve adhesion by making the film more easily wetted. Alternatively, as shown in FIG. 12, material may be extruded directly onto the outer surface of the screen atop layer of substance 38.

As forming screen 32 rotates past idler roll 36, heat from a radiant heat source 44 or other heat source may be useful to soften material web 42 for vacuum thermoforming. Polymer films are most easily thermoformed, whereas other materials such as foils or papers may best be embossed or hydraulically formed, wherein heating the material prior to forming may not be advantageous.

Meanwhile, layer of substance 38 is transferred from the drum to the material web. A vacuum manifold 46 operates with forming screen 32 so as to draw material web 42 around layer of substance 38 and into recesses in forming screen 32 to form protrusions similar to protrusions 14.

Alternatives to heat and vacuum for forming protrusions in a material web are well known in the art. For example, by applying heated compressed gas to the non-substance side of the web of deformable film while the material web rests against the forming screen, protrusions may be created. Also, mechanically embossing the material web against the forming screen provides yet another forming method for use with female forming structures.

As forming screen 32 rotates, vacuum thermoforming, hydraulic forming, embossing, or combinations thereof, are completed and a formed material web 43 is thereafter discharged around a discharge idler roll 48. Automated process 30 may also have a sprayer 50 located upstream of substance application system 34. Sprayer 50 may be used for applying a renewable release agent to outer surface 40 so that substance 38 will be preferentially attracted to material web 42. Alternatively, a permanent release agent may be applied to outer surface 40 to alleviate the need for sprayer 50.

FIGS. 6–10 show steps of a preferred laboratory method of making discrete pieces of material 10, which is preferably a thin thermoplastic film containing a pressure sensitive adhesive substance. The method is generally indicated as 60.

Figures 6, 7, 8:
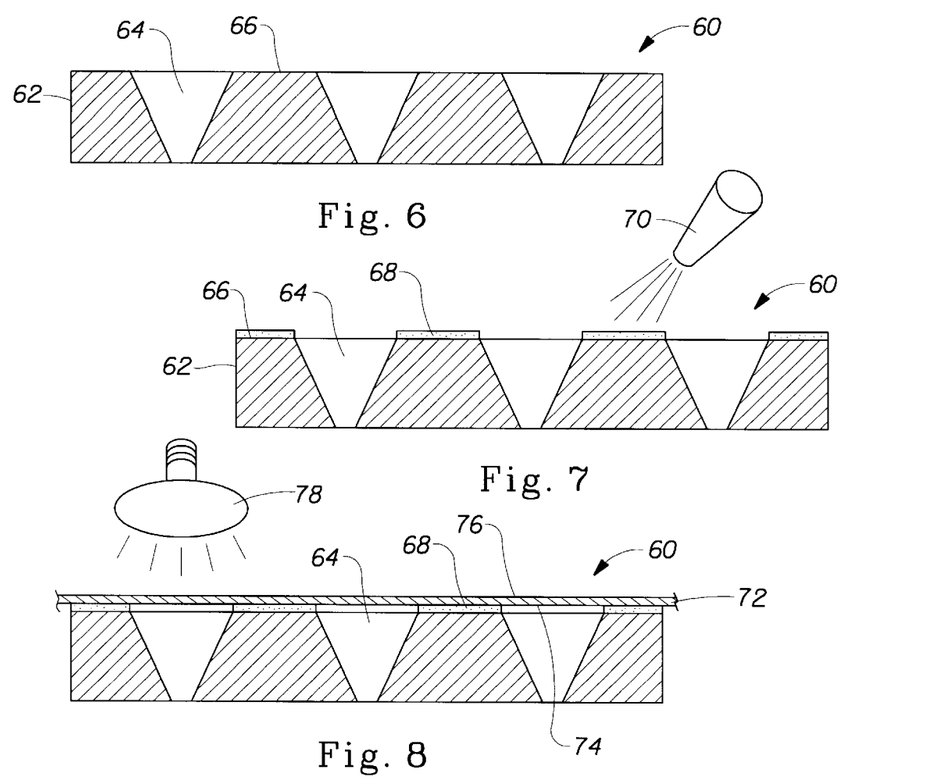
FIG. 6 is a sectioned elevation view of a forming screen used for making the three dimensional material surface of the present invention, disclosing tapered recesses into which protrusions are formed.
FIG. 7 is a sectioned elevation view thereof, disclosing substance sprayed onto a top surface of the forming screen, such that the substance does not bridge the recesses in the top surface.
FIG. 8 is a sectioned elevation view thereof, showing a piece of material laid on top of the layer of substance and being exposed to heat from an infrared source on the side opposite the substance side.

As shown in FIG. 6, method 60 utilizes a forming screen 62, which has a plurality of conical recesses 64, about 0.025 inches (0.064 cm) in diameter at the larger end. Recesses 64 are preferably photoetched into forming screen 62, which is preferably a stainless steel sheet, about 0.006 inches (0.015 cm) to 0.012 inches (0.030 cm) thick. Forming screen 62 has a top surface 66, which is preferably coated to provide release properties for an adhesive substance.

Conical recesses 64 may have sidewalls which have cone angles which vary from 0° to 60°. That is, the recesses may have straight sidewalls or tapered sidewalls. Straight sidewalls might be found, for example, in screens which have punched holes therein. Methods of making metal screens by photoetching are described in more detail in commonly owned U.S. Pat. No. 4,342,314 to Radel and Thompson, U.S. Pat. No. 4,508,256 to Radel et al., and U.S. Pat. No. 4,509,908 to Mullane, Jr., which are hereby incorporated herein by reference.

FIG. 7 shows a substance 68 sprayed onto top surface 66 by sprayer 70. Substance 68 may be a latex emulsion which is a pressure sensitive adhesive when dried. Drying is achieved by application of warm air or radiant heat, for example. The preferred hot melt adhesive is applied to top surface 66 by transfer coating, as shown in FIG. 5. Some substances may not require drying, such as powders or microencapsulated liquids. Substance 68 preferably does not bridge the recesses, but instead remains only on top surface 66 between recesses. Applying a low level vacuum through recesses 64 during spraying of the substance onto top surface 66 helps to avoid substance bridging of recesses 64.

FIG. 8 shows an exemplary piece of material 72, made of 0.0003 inch (0.0076 mm) to 0.001 inch (0.025 mm) nominal thickness high density polyethylene, laid on top of a dried latex emulsion or a hot melt adhesive coating. High density polyethylene is preferred over low density polyethylene because the former can be made thinner for the same protrusion deforming strength and because once deformed, HDPE protrusions do not tend to rebound toward their undeformed initial configuration as do the LDPE protrusions. Preferably, piece of material 72 has a substance side 74 which has been treated for maximum adhesion to substance 68. It also has a non-substance side 76 facing outward. In order to initiate thermoforming of piece of HDPE material, the film is heated by an infrared heating lamp 78 or by hot air from non-substance side 76. Heating by heating lamp may occur for approximately 60 seconds until the piece of HDPE film is heated to about 200° F. (93° C.) to 300° F. (149° C.).

Figure 9:
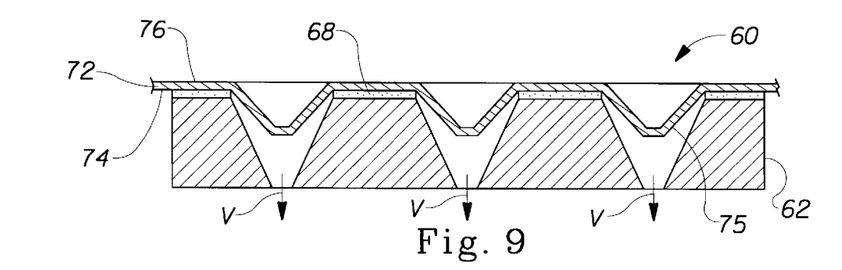
FIG. 9 is a sectioned elevation view thereof, showing vacuum applied through the recesses to draw the heated material into the recesses to form hollow protrusions in the material between the pattern of substance.
Figure 10:
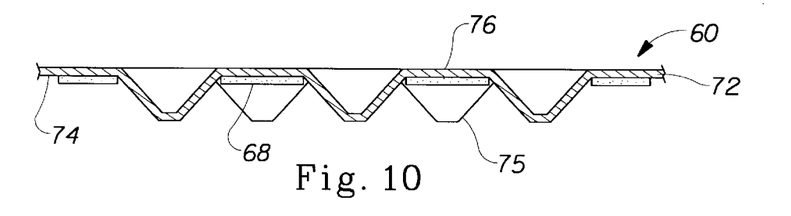
FIG. 10 is a sectioned elevation view thereof, showing the forming screen removed, leaving the substance layer attached to the material between the protrusions.

Immediately after heating piece of material 72, as shown in FIG. 9, vacuum V is applied from a vacuum source (not shown) to recesses 64 at their open ends. Preferably, vacuum V is approximately 20 inches of mercury (68 kPa). Vacuum V draws portions of softened material 72 lying above recesses 64 down into recesses 64 to form protrusions 75. When piece of material 72 is allowed to cool, it remains formed into formed material 73. Formed material 73 is removed from forming screen 62, as shown in FIG. 10. Because of preferential adhesion, substance 68 stays attached to piece of formed material 73. The piece of material is thereby thermoformed to generate conical protrusions with truncated cone or domed outermost ends. The outermost ends preferably extend approximately 0.003 inches (0.076 mm) to 0.011 inches (0.279 mm) beyond the surface of layer of substance 68. Protrusion shapes other than conical may be produced by different shaped screen recesses. Recesses may be pyramidal, hemispherical, cylindrical, polygonal, and elongated, for example; however, the conical shaped protrusion is believed to provide substantially consistent inverting and/or crushing resistance. Recesses may be formed to produce different shapes and sizes and heights of protrusions within a given pattern, but again it is generally desired that protrusions be uniform so that the deformation force is predictable and consistent.

Protrusion shape has also been found to influence the stacking of material sheets or the rolling of material webs into rolls. If the same protrusion shape repeats over and over on the same spacing, for example, adjacent material sheets in a stack and adjacent layers in a roll tend to nest together, thereby negating the benefit of standoffs in protecting the substance internal to the standoffs. For situations where nesting is an issue, non-uniformly shaped or sized or spaced protrusions may be advantageous over a regular pattern of conical protrusions. Non-uniformly shaped or sized or spaced protrusions are disclosed in a commonly assigned, co-pending U.S. patent application, filed concurrently with the present application on Nov. 8, 1996 having Attorney docket number 6356 and USPTO Ser. No. 08/745,339.

Because the same common forming screen is used to transfer the substance to the material as is used to form the protrusions, the substance pattern is conveniently registered with the protrusions. In the preferred embodiment, the top surface 66 of forming screen 62 is continuous except for recesses 64; thus, the substance pattern is totally interconnected in this configuration. However, if a discontinuous pattern of substance were coated onto forming screen 62, a discontinuous substance pattern between protrusions would result.

It is believed that the protrusion size, shape and spacing, the web material properties such as flexural modulus, material stiffness, material thickness, hardness, deflection temperature as well as the forming process determine the strength of the protrusion. The forming process is important in polymer films for example, since "cold forming" or embossing generates residual stresses and different wall thickness distributions than that produced by thermoforming at elevated temperatures. For some applications it is desirable to provide a stiffness (deformation resistance) which is sufficient to withstand a pressure of at least 0.1 pounds per square inch (0.69 kPa) without substantially deforming protrusions to where the substance contacts an external surface. An example of this requirement would be the need to wind the web onto a roll for transport and/or dispensing. Even with very low in-wound pressures of 0.1 pounds per square inch (0.69 kPa), a residual in-wound pressure in the interior of the roll may deform protrusions in the web sufficiently to bring the overlaying web layers into contact with the substance. A "threshold" protrusion stiffness is required to prevent this winding damage from occurring. Similarly, when the web is stored or dispensed as discrete sheets, this "threshold" stiffness is required to prevent premature activation of the product due to the weight of overlaying layers of sheets or other forces, such as forces induced by shipping vibrations, mishandling, dropping and the like.

Figure 11:
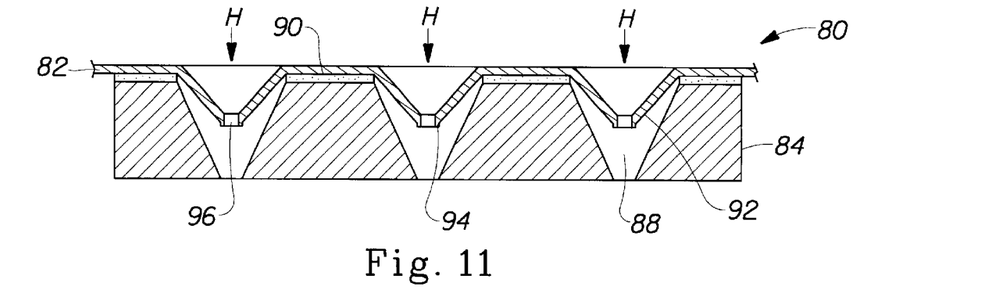
FIG. 11 is a sectioned elevation view similar to FIG. 9, showing hydraulic formation replacing vacuum forming, and outermost ends of protrusions being apertured.

FIGS. 11 through 16 show alternatives to the method and material described hereinbefore. In FIG. 11 there is shown a method of forming a material, generally indicated as 80. Method 80 has a deformable material 82 placed onto a forming screen 84. Forming screen 84 has a top surface 86 and recesses 88. Top surface 86 is coated with a substance 90 such that substance 90 does not bridge recesses 88. Material 82 is placed on top of substance 90 as in the embodiment illustrated by FIGS. 8 and 9. However, FIG. 11 shows a positive pressure forming force H applied to material 82 from above the screen instead of a vacuum force applied from below the screen. Forming force H may originate from a liquid applied under pressure against material 82, such as occurs in hydraulic forming. Forming force H may also be generated by application of a pressurized gas, perhaps heated. A preferred fluid for use in a positive pressure forming application is heated water, the use of which is described in greater detail in commonly assigned U.S. Pat. No. 4,695,422 to Curro et al., U.S. Pat. No. 4,778,644 to Curro et al., and U.S. Pat. No. 4,839,216 to Curro et al., which are hereby incorporated herein by reference.

FIG. 11 also shows material 82 deformed to generate protrusions 92. Protrusions 92 have outermost ends 94. Although not required in many applications of the material of the present invention, each outermost end has an aperture 96 therein, so that the resulting material may provide breathability and/or substance permeability. Ideally, apertures 96 are sized in a range of 0.001 inch (0.025 mm) diameter to 0.039 inch (1.000 mm) diameter.

FIG. 12 discloses an alternative process generally indicated as 100. Process 100 is similar to process 30 illustrated in FIG. 5. Process 100 has forming screen 102, which is curved to form a drum. A substance source and application system 104 are positioned upstream of an extruder 106. Substance application system 104 deposits a thin coating of a substance 108 onto an outer surface 110 of forming screen 102. Outer surface 110 is treated to have a low critical surface tension so that substance 108 will preferentially adhere to a material introduced onto substance 108 rather than to outer surface 110 when substance 108 is dried or cooled. Process 100 is different from process 30 in that a material 112 is created by directly extruding material 112 onto forming screen 102 instead of metering a preformed web thereon. Material 112 is laid on top of layer of substance 108 and material 112 has a greater affinity for substance 108 than does outer surface 110, so that substance 108 is effectively transferred to material 112 when contact between them occurs.

As forming screen 102 rotates past extruder 106, material 112 is formed as shown in FIG. 11, but preferably without apertures. A vacuum manifold 116 is illustrated with forming screen 102 so as to draw material 112 around layer of substance 108 and into recesses in forming screen 102 for forming hollow protrusions. Once formed, hollow protrusions preferably pass under an "ink jet" type substance injection delivery system 120, which deposits a spot of substance 122 into the depression of each hollow protrusion from outside forming screen 102, resulting in a formed material 121. Although registration is required between substance injection system 120 and the hollow protrusions, system 120 may be registered directly from the recesses in forming screen 102, which define the location of the protrusions. This is much less difficult than would be registration with a transient web of material, particularly very thin webs. Formed material 121 is thereafter discharged around a discharge idler roll 118.

Figure 13:
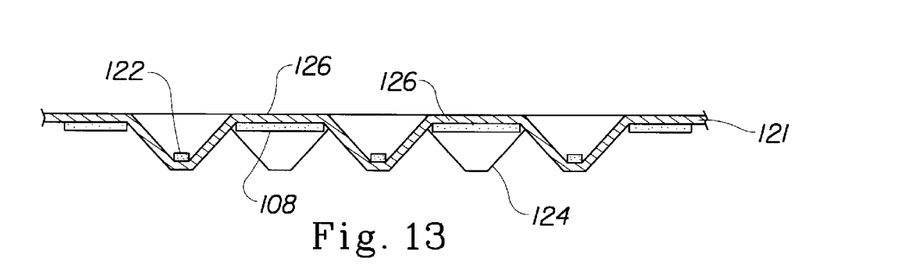
FIG. 13 is a sectioned elevation view of the material resulting from the method of FIG. 12, showing the forming screen removed, and substance portions attached to both sides of the formed material, both substances being protected by the same standoff protrusions.
Figure 14:
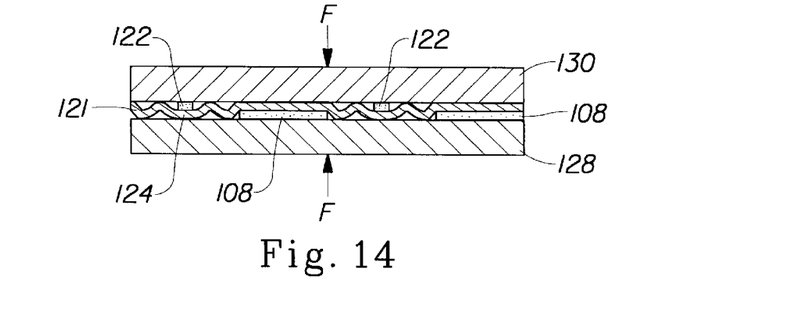
FIG. 14 is a sectioned elevation view, similar to FIG. 4, showing the effect of pressing the material of FIG. 13 between two external surfaces, such that protrusions deform by substantially inverting and/or crushing to allow the substance layer between protrusions and the discrete substance portions within protrusions to contact the target surfaces.

FIG. 13 shows formed material 121 after it leaves process 100. Formed material 121 has protrusions 124 and valleys 126 surrounding protrusions 124. Located in valleys 126 is preferably an interconnected, continuous layer of substance 108. Although, as described earlier, a discontinuous application of substance to the forming screen results in a discontinuous pattern of substance on material 121. Inside depressions of hollow protrusions 124 are discrete spots of substance 122. Substance 108 and substance 122 may be the same, such as a pressure sensitive adhesive. If a pressure sensitive adhesive, substances 108 and 122 are on opposite sides of formed material 121, protected from contact with surfaces adjacent to material 121. In this situation, the formed material together with adhesive 108 and 122 may function as a double-sided tape. FIG. 14 illustrates how formed material 121 could behave if contacted on both sides by external surfaces 128 and 130 under force F. Protrusions 124 deform by substantially inverting and/or crushing and thereby position substance 108 in contact with surface 128 and substance 122 in contact with surface 130. Substances 108 and 122 could be distinctly different from each other and serve different purposes, however.

If the three dimensional structure of the present invention is used as a tape or a storage wrap, for example, the external contact surfaces may be either compliant or rigid and planar or non-planar. Having the three dimensional structure deform is preferred for use with a rigid target surface. If the substance is adhesive and the objective is releasable adherence to a target surface after deformation of the structure, then degree of adhesion is important. For a storage wrap where releasability after adhesion is necessary, the peel strength of the adhesive is preferably measured by Pressure Sensitive Tape Council Method PSTC-1. A 12 inch (30.5 cm) long by 1 inch (2.5 cm) wide strip of film is rolled once against a smooth stainless steel surface at a rate of 12 inches (30.5 cm) per minute using a 4.5 pound (2.04 kg) roller and then tested as having a peak adhesion value ranging from about 1 ounces/inch to about 50 ounces/inch of strip width and more preferably from about 1 to about 2.5 ounces/inch (0.012 to 0.027 kg/cm) of strip width.

Minimum adhesion which maintains a seal is desired for a storage wrap, so that the wrap is easily peeled open for access to the stored item(s). Inversion of protrusions, especially those made of HDPE, minimizes protrusion spring back so that higher adhesion isn't necessary in order to prevent the failure of relatively weak seals. In this embodiment it is desired that the protrusion remain "dead" or non-resilient after being inverted or crushed; however, a resilient protrusion could be used, for example, where it is intended for the bond to be permanent, where aggressive adhesive overcomes spring back. Also, a resilient protrusion may be desirable where repeat use of the material is intended.

Figure 15:
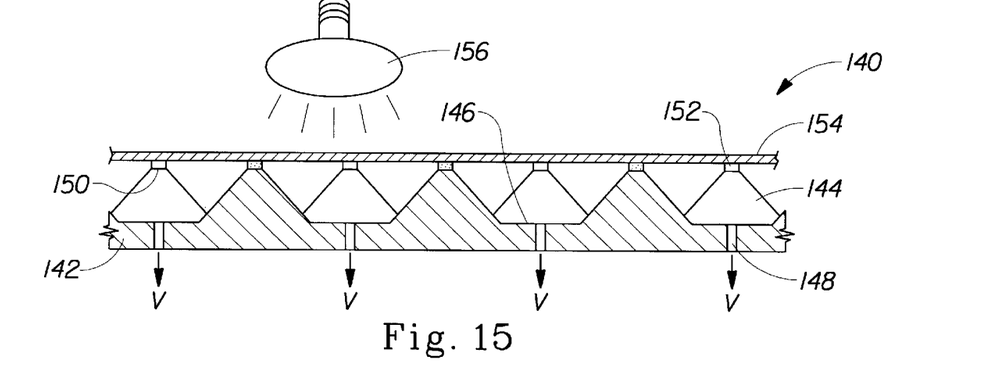
FIG. 15 is a sectioned elevation view of an alternative method of making a material, similar to FIGS. 8 and 9, except that conical pins instead of openings in a screen provide an inverse of the material of FIG. 10; that is, substance is transferred into the hollow protrusions instead of into valleys between protrusions, when the material is formed over the substance-coated pins.
Figure 16:
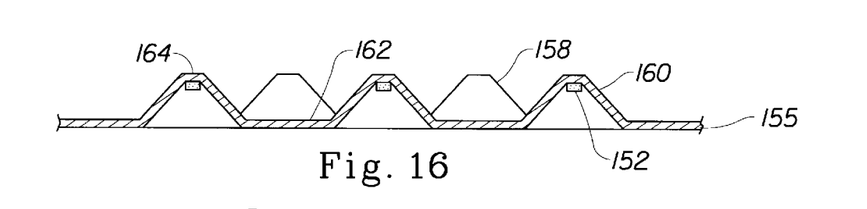
FIG. 16 is a sectioned elevation view of the material which results from the method of FIG. 15.

FIGS. 15 and 16 illustrate another alternative process for making the material of the present invention, generally indicated as 140. Process 140 has instead of a forming screen a forming plate 142 with pins 144 projecting outwardly therefrom. Pins 144 are preferably conical and are spaced apart by valleys 146. At the base of each valley 146 is an aperture 148 through forming plate 142. Aperture 148 may be used to draw a vacuum V between pins 144 in order to form a deformable piece of material over the pins. Hydroforming and embossing offer alternative forming means for causing the material to conform to a male forming structure.

FIG. 15 shows pins 144 having outer ends 150 coated with a substance 152. Atop substance 152 is placed a piece of deformable material 154, which has a greater attraction for substance 152 than outer ends 150 of pins 144. Outwardly of material 154 is shown a heat generating lamp 156, which may be used to heat material 154 in order to condition it for vacuum forming if material 154 is a polymer film, for example. The result of vacuum forming material 154 is shown in FIG. 16, with forming plate 142 removed. The result is formed material 155. A plurality of conical protrusions 158 are formed over pins 144 when vacuum pulls material 154 down into valleys 146. Other pin shapes besides conical produce correspondingly shaped protrusions. Pin shapes such as pyramidal, hemispherical, cylindrical, polygonal, and elongated bumps are also possible; however, the conical shape is believed to provide a substantially predictable and consistent inverting and/or crushing resistance in protrusions. Pins can also be different shapes and sizes and heights within a given pattern, but again it is generally desired that resulting protrusions be uniform so that the deformation force is predictable and consistent.

Substance 152 is transferred to the inside of protrusions 158 when they are formed. Wherever a material is vacuum formed, the sidewalls 160 of protrusions 158 are thinned compared to the original thickness of the material placed over the pins. A portion of the material 162, which is drawn into the valleys 146 between pins 144, may also be thinned; however, another portion 164, which remains in contact with substance 152 at outer ends 150 typically does not become substantially thinned by the process 140. This is believed due to material friction at the edges of the outer ends of the pins.

In process 140, portion of material 162 between protrusions is formed and may therefore be thinned, whereas in processes 60 and 100, it is protrusions 75 and 92, respectively, which are formed and may therefore be thinned.

It has been discovered while reducing to practice the present invention that when using hot melt adhesive for the substance, thermoforming behaves differently than when other substances are processed. The difference is that protrusions, which are formed when hot melt adhesive has been applied to the forming surface, tend to exhibit more thinning in their sidewalls. It is believed that the hot melt adhesive cools and solidifies when contacting the metal forming surface and thereby prevents web material in contact with the adhesive from being drawn into the recesses, so that uniform thickness valleys result. With other substances, such as latex adhesive, less thinning of protrusion sidewalls occurs, presumably because some of the web material in contact with the adhesive on the lands or pin tops of the forming surface flows into the recesses during thermoforming.

Figure 17:
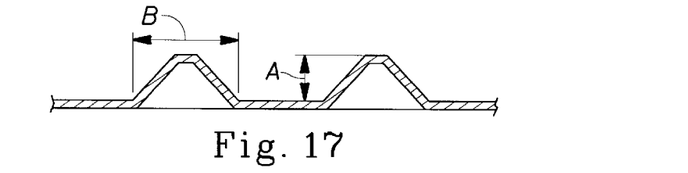
FIG. 17 is a sectioned elevation view of the material formed by the method of FIGS. 8 and 9 or by the method of FIG. 15, showing preferred dimensional relationships of protrusions.

FIG. 17 shows a preferred shape of the protrusions and valleys of the present invention, which enables protrusions to substantially invert and/or crush as a mode of deforming. The preferred shape minimizes protrusion fold-over and interference with substance placed in valleys between protrusions, or inside hollow protrusions, or both. Also, the preferred shape helps to ensure a repeatable, predictable, resistance to protrusion deformation. FIG. 17 shows that each protrusion is defined by a height dimension A and a base diameter dimension B. A preferred ratio of base diameter B to height A, which enables protrusions to substantially invert and/or crush without fold-over, is at least 2:1.

Deformation mode and force can be influenced by the sidewall thickness profile to provide more desired results. A protrusion's sidewall connects the outermost portion of the protrusion to the unformed material adjacent to base perimeter of the protrusion. The sidewall as defined may also contain a peripheral region substantially within the outermost portion which is substantially thinner than the interior region of the outermost portion. Protrusions where at least a portion of the sidewalls are substantially thinner than the unformed material adjacent to the base perimeter are believed preferred for deformation by the user. Sidewalls that are also substantially thinner in at least a portion of the sidewall as compared to the material at the outermost portion of the protrusion also beneficially bias the deformation to occur primarily within the sidewall structure.

In structures containing relatively small protrusions, as found in high number density protrusion patterns, such thinner sidewall gauges can be particularly useful.

Methods of production can influence the sidewall thickness profile such as in the use of a forming screen with essentially straight screen walls which define the forming screen hole. Such a process allows for substantially thinner sidewall thickness since the protrusion is freely drawn from the base perimeter into the forming screen recess to the point of contact with the internal backup screen. The internal backup screen's purpose is to prevent further drawing of the protrusion. This approach yields a more varied gauge profile within the sidewalls.

Figure 18:
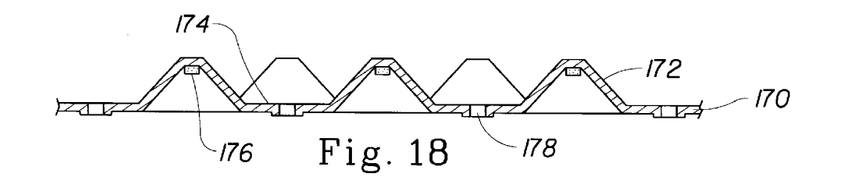
FIG. 18 is a sectioned elevation view of an alternative material made from the method of FIG. 15, which results in a material similar to that of FIG. 16, except that apertures are made in valleys of the material between protrusions.

FIG. 18 shows an alternative to the material of FIG. 16, also preferably made by the process of FIG. 15. A material 170 has hollow protrusions 172 surrounded by interconnected valleys 174. Inside hollow protrusions 172 are spots of a substance 176. The difference between the material of FIG. 16 and that of FIG. 18 is the addition of apertures 178 in valleys 174, shown in FIG. 18. Apertures 178 may be made, for example by applying the forming force H of FIG. 11 to the forming method illustrated in FIG. 15 in place of heat lamp 156 and vacuum force V.

Figure 19:
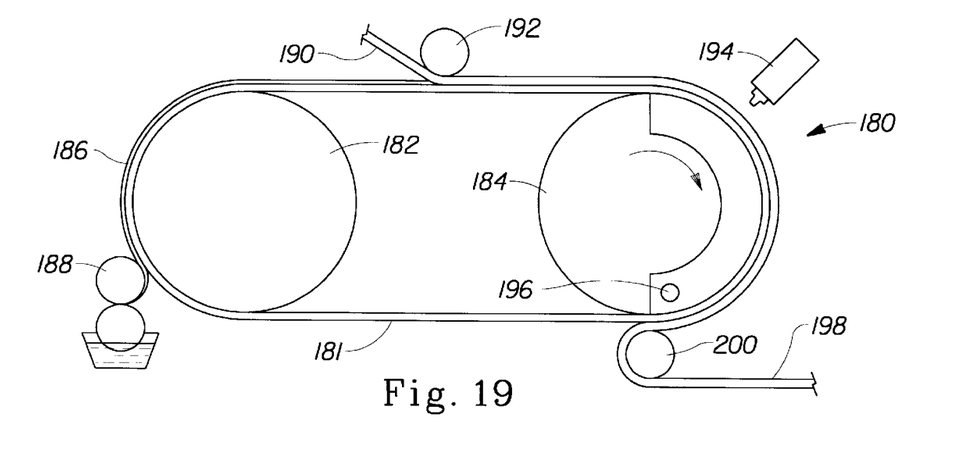
FIG. 19 is a schematic view of an alternative method of making a material of the present invention, showing a forming screen as a belt wrapped around a vacuum drum and a drive pulley.

FIG. 19 shows a most preferred method of making a material similar to material 10 of the present invention, which is generally indicated as 180. The formed material is preferably transparent or translucent, so that it may be accurately positioned before being deformed. Transparency, however, introduces a new problem of determining on which side of the three dimensional structure the substance is located, in order to know which side to place against a target surface. Substance side identification can be solved by placing indicia on the surface of the three dimensional structure, by coloring the substance a different tint than the three dimensional structure, or by providing a laminated material structure of different tints, for example. In the case of labels, transparency may not be needed since material edges may be used for proper positioning.

Micro-texturing the material during forming may also be useful, such as in producing a distinction between one side of the material and the other side. Micro-texturing of the outermost surface features of the three dimensional structure may be achieved in the present invention, for example, by drawing the piece of material into forming screen recesses and against a micro-textured surface, such as a vacuum drum having tiny apertures therein.

Forming screen 181 is threaded over idler pulley 182 and a driven vacuum roll 184. Forming screen 181 is preferably a 0.005 inch (0.013 cm) thick, 12.5 inch (31.8 cm) wide, 6 foot (183 cm) circumference stainless steel belt, having the desired protrusion pattern etched as recesses in the belt. Covering the outer surface of vacuum roll 184 is a 195 mesh seamless nickel screen having a diameter of 8.63 inches (21.9 cm), which serves as a porous backing surface for forming screen 181.

For producing a pressure sensitive adhesive containing material, a substance 186, preferably hot melt adhesive, is coated onto forming screen 181 by a substance applicator 188 while forming screen 181 travels at about 20 feet (610 cm) per minute. A material 190, for example, a HDPE film web about 0.0005 inches (0.0013 cm) thick, is brought into contact with the substance coated forming screen at material infeed idler roll 192. Hot air at approximately 600° F. (316°

C.) and flowing at approximately 11.25 SCFM (0.32 cubic meters/minute) is directed radially at material 190 by a hot air source 194 as the material passes over vacuum roll 184 and as vacuum is applied to forming screen 181 through vacuum roll 184 via fixed vacuum manifold 196 from a vacuum source (not shown). A vacuum of approximately 12 inches of mercury (40.6 kPa) is applied as the material is heated by hot air source 194. A formed, substance coated material 198 is stripped from forming screen 181 at stripping roll 200.

Stainless steel forming screen 181 is a fabricated, seamed belt. It is fabricated in several steps. The recess pattern is developed by computer program and printed onto a transparency to provide a photomask for photoetching. The photomask is used to create etched and non-etched areas. The etched material is typically stainless steel, but it may also be brass, aluminum, copper, magnesium, and other materials including alloys. Additionally, the recess pattern may be etched into photosensitive polymers instead of metals. Examples are described along with a methods of making polymer forming screens in commonly owned U.S. Pat. No. 4,514,345 to Johnson et al., U.S. Pat. No. 5,098,522 to Smurkoski et al., U.S. Pat. No. 4,528,239 to Trokhan, and U.S. Pat. No. 5,245,025 to Trokhan, which are hereby incorporated herein by reference.

Next, the forming screen is converted into a continuous belt by butt welding the ends together, using either laser or electron beam welding. This produces a nearly undetectable seam, which is needed to minimize disruptions in the recess pattern. The final step is coating the endless belt with a low critical surface tension (non-stick) coating, such as a Series 21000 material by Plasma Coatings of TN, Inc., hereinbefore described. This coating allows the formed material to be removed from the belt without undue stretching or tearing.

A belt forming screen is believed advantageous to a flat plate or a drum forming screen because a belt enables screen patterns and pattern lengths to be changed more easily and larger patterns may be used without having massive rotating members.

In general, the present invention is a three dimensional structure for holding a substance protected from inadvertent contact with external surfaces. The structure is convertible to a substantially two dimensional structure by applying a compressive force so that the structure collapses to release or expose the substance into contact with external surface(s). However, the scope of the invention also applies to three dimensional structures holding substances from inadvertent contact, which are converted to substantially two dimensional structures by means other than compression. For example, the inventors have found that a tensile force applied to the same three dimensional structure can cause it to plastically deform longitudinally and thereby contract in caliper or thickness to similarly expose or release substance. It is believed that under sufficient tension, the material between protrusions deforms in response to forces in the plane of the material and that protrusions are thereby elongated in the same direction. When the protrusions are elongated, they are reduced in height. With enough elongation the protrusions are reduced in height to where the substances between them, in them, or both are exposed.

For a one inch wide strip of material 10, made from 0.0003 inch (0.0076 mm) thick HDPE and formed to have protrusions of 0.006 inches (0.152 mm) height and 0.030 inches (0.762 mm) diameter, spaced 0.045 inches (1.143 mm) apart, the tensile force found necessary to cause protrusions to expose a 0.001 inch (0.025 mm) thick coating of adhesive in the valleys between protrusions is approximately 0.80 pounds (0.36 kg) per inch of strip width.

A combination of compression and tensile forces may be applied to the material of the present invention in order to expose a substance from within the three dimensional structure. Although in a preferred embodiment of the present invention, the tensile force necessary to achieve sufficient deformation of said three dimensional structure in order to expose substance to an external surface is significantly greater than a compressive force to achieve the same result, a structure may be designed which is more easily deformed by a tensile force applied in a specific planar direction. For example, a structure may have parallel waves instead of protrusions and the waves may be easily flattened by stretching the structure perpendicular to the waves but in the plane of the waves. Other suitable tensile response structures are disclosed in U.S. Pat. No. 5,518,801 to Chappell et al. which is hereby incorporated herein by reference.

In another example, heat could be applied to cause the same structure made of shrinkable film to reduce in thickness to similarly release or expose the substance.

Examples of uses of the three dimensional structure of the present invention besides tapes, labels, and storage wraps include: lotion impregnated facial tissues, scented strips containing microencapsulated perfumes, adhesive impregnated shelf and wall paper, medicinal patches, patterned condiment delivery to a surface, two component adhesives, laundry pre-treating chemicals, abrasive delivery systems, and other applications where avoidance of contact with a substance held in a substrate is desired until some action is taken.

As described hereinafter, different substances can be deposited on the opposing faces of the formed material. Multiple substances can be located on the same face of the material either geometrically spaced from each other or commingled. Substances can be partially layered. An example is a layer of adhesive adjacent to the material surface with a solid particulate adhered to the exposed side of the adhesive layer.

A pattern of protrusions can be superimposed either on a similar dimensional scale or on a different dimensional scale such as a single or multiple "microprotrusion" pattern located on the tops of other larger protrusions.

While particular embodiments of the present invention have been illustrated and described, it will be obvious to those skilled in the art that various changes and modifications may be made without departing from the spirit and scope of the invention, and it is intended to cover in the appended claims all such modifications that are within the scope of the invention.

What is claimed is:

1. A method of making a three dimensional structure having outermost surface features and having spaces for containing a substance internal to said outermost surface features such that said substance is protected from inadvertent contact with external surfaces, said method comprising the steps of coating a substance onto a forming surface, applying a piece of material to the substance coated forming surface, transferring said substance from said forming surface to said piece of material, and forming said piece of material into a three dimensional structure on said forming surface while said substance is in contact with said forming surface, in order to accurately register said three dimensional structure with said substance.

2. The method of claim 1 wherein said spaces of said three dimensional structure are interconnected so that substance transferred thereto is continuous.

3. The method of claim 1 further comprising the step of providing said forming surface with a low critical surface tension.

4. The method of claim 3 wherein said low critical surface tension is about 18 dynes/cm.

5. A method of making a material having a substance protected from inadvertent contact with an external surface until said material is deformed, said method comprising the steps of:

a) coating a forming surface with a first substance;

b) introducing a piece of material having a first side and a second side onto said forming surface such that said first side is in contact with said first substance on said forming surface, said first substance preferentially adhering to said first side of said piece of material; and c) forming said piece of material to create a three dimensional structure having a plurality of hollow protrusions spaced apart by valleys, said first substance being transferred from said forming surface into said three dimensional structure accurately registered with said three dimensional structure by using a common transfer and forming surface.

6. The method of claim 5 wherein said forming surface comprises a forming screen having a top surface and a plurality of recesses therein and wherein said plurality of hollow protrusions are formed into said recesses.

7. The method of claim 6 further comprising the step of providing said top surface of said forming screen with a low critical surface tension.

8. The method of claim 5 wherein said forming surface comprises a forming plate having pins extending therefrom, said pins having top surfaces and spaces therebetween, and wherein said plurality of hollow protrusions are formed over said pins.

9. The method of claim 8 further comprising the step of providing said top surfaces of said pins with a low critical surface tension.

10. A method of making a material having a substance protected from inadvertent contact with an external surface until said material is deformed, said method comprising the steps of:

a) coating a forming screen with a first substance, said forming screen having a top surface and a plurality of recesses therein, said coating step applying said first substance to said top surface without bridging said recesses;

b) introducing a piece of material having a first side and a second side onto said forming screen such that said first side is in contact with said first substance on said top surface of said forming screen, said first substance preferentially adhering to said first side of said piece of material; and c) forming said piece of material to create a plurality of hollow protrusions extending from said first side into said recesses of said forming screen, said plurality of hollow protrusions being spaced apart by valleys into which said first substance is transferred from said forming screen, said plurality of hollow protrusions being accurately registered with said first substance by use of a common transfer and forming surface, said piece of material having a plurality of depressions on said second side corresponding to said plurality of hollow protrusions.

11. The method of claim 10 further comprising the step of providing said top surface of said forming screen with a low critical surface tension.

12. The method of claim 11 wherein said low critical surface tension is about 18 dynes/cm.

13. The method of claim 10 wherein said first substance forms an interconnected layer in said valleys between said protrusions.

14. The method of claim 10 further comprising the step of forming an aperture at said outermost end of each of said plurality of protrusions.

15. The method of claim 10 further comprising the step of injecting a second substance into said plurality of depressions on said second side of said piece of material.

16. The method of claim 10 wherein said step of introducing said piece of material onto said forming screen comprises extrusion of said piece of material directly onto said forming screen.

17. A method of making a material having a substance protected from inadvertent contact with an external surface until said material is deformed, said method comprising the steps of:

a) coating top surfaces of pins extending from a forming plate with a first substance, said pins being separated from each other by spaces, said coating step applying said first substance to said top surfaces of said pins without bridging across said spaces;

b) introducing a piece of material having a first side and a second side onto said pins such that said first side is in contact with said first substance on said top surface of said pins, said first substance preferentially adhering to said piece of material; and c) forming over said pins of said forming plate said piece of material to create a plurality of hollow protrusions extending from said second side, said plurality of hollow protrusions having insides registered with said pins which have discrete spots of said first substance thereon, said piece of material having an interconnected valley formed on said second side corresponding to said spaces between said pins.

18. The method of claim 17 further comprising the step of providing said top surfaces of said pins with a low critical surface tension.

19. The method of claim 18 wherein said low critical surface tension is about 18 dynes/cm.

20. The method of claim 17 wherein said step of introducing said piece of material onto said pins comprises extrusion of said piece of material directly onto said top surface of said pins.

21. The method of claim 17 further comprising the step of forming an aperture in said interconnected valley between each of said plurality of protrusions.

* * * * *